US00PP30163P2

(12) United States Plant Patent
Bean

(10) Patent No.: US PP30,163 P2
(45) Date of Patent: Jan. 29, 2019

(54) ***AGAPANTHUS* PLANT NAMED 'MP003'**

(50) Latin Name: ***Agapanthus* hybrid**
Varietal Denomination: MP003

(71) Applicant: Charles Andrew de Wet, Johannesburg (ZA)

(72) Inventor: Quinton Bean, Johannesburg (ZA)

(73) Assignee: Charles Andrew de Wet, Johannesburg (ZA)

( * ) Notice: Subject to any disclaimer, the term of this patent is extended or adjusted under 35 U.S.C. 154(b) by 0 days.

(21) Appl. No.: 15/732,583

(22) Filed: Nov. 29, 2017

(51) Int. Cl.
*A01H 5/02* (2018.01)

(52) U.S. Cl.
USPC ..... Plt./398

(58) Field of Classification Search
USPC ..... Plt./398
See application file for complete search history.

*Primary Examiner* — Annette H Para
(74) *Attorney, Agent, or Firm* — Penny J. Aguirre

(57) ABSTRACT

A new cultivar of *Agapanthus*, 'MP003', that is characterized by flowers that are vivid purple in color, its fast growth habit, its extended blooming period with re-bloom throughout the year, and its good resistance to root and crown rot caused by *Fusarium* sp. and soft rot caused by *Erwinia* sp.

2 Drawing Sheets

Botanical classification: *Agapanthus* hybrid.
Varietal denomination: 'MP003'.

BACKGROUND OF THE INVENTION

The present invention relates to a new and distinct cultivar of *Agapanthus* of hybrid origin and will be referred to hereafter by its cultivar name, 'MP003'. 'MP003' represents a new perennial grown for landscape use.

The new cultivar was derived from a controlled breeding program by the Inventor in Hartebeespoort, Northwest Province, South Africa. The objective of the breeding program was to develop a new cultivar of *Agapanthus* that had a more compact pant habit combined with purple flowers and a vigorous growth habit. The Inventor made a cross in November of 2008 between unnamed proprietary plants of *Agapanthus* from the Inventor's breeding program as both the female parent and male parent. The Inventor selected 'MP003' in November of 2012 (first selected in 2010 for further evaluation) as a single unique plant amongst the seedlings that resulted from the above cross.

Asexual propagation of the new cultivar was first accomplished by division by the Inventor in Hartebeespoort, Northwest Province, South Africa in January of 2013. Asexual propagation by division and tissue culture has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'MP003' as a distinct cultivar of *Agapanthus*.

1. 'MP003' exhibits flowers that are vivid purple in color.
2. 'MP003' exhibits a fast growth habit.
3. 'MP003' exhibits an extended blooming period with re-bloom throughout the year.

4. 'MP003' exhibits good resistance to root and crown rot caused by *Fusarium* sp. and soft rot caused by *Erwinia* sp.

The female parent of 'MP003' differs from 'MP003' in having flowers that are pale purple in color. The male parent of 'MP003' differs from 'MP003' in having lower inflorescence production and a taller plant height. 'MP003' can be most closely compared to the *Agapanthus* cultivars 'Purple Delight' (not patented) and 'Amethyst' (not patented). 'Purple Delight' and 'Amethyst' are similar to 'MP003' in having flowers that are purple in color. 'Purple Delight' differs from 'MP003' in having a slower growing habit, pale purple flower color and less inflorescence production and re-blooming. 'Amethyst' differs from 'MP003' in having flowers that are pale purple in color, a smaller plant size and less re-blooming.

BRIEF DESCRIPTION OF THE DRAWINGS

The accompanying colored photographs illustrate the overall appearance and distinct characteristics of the new *Agapanthus*. The photographs were taken of plants about 2 years in age (from a bare root division) of 'MDB001' as grown outdoors in a 3-gallon container in Hartebeespoort, Northwest Province, South Africa.

The photograph in FIG. 1 provides a side view of a plant of 'MP003' in bloom.

Figure 1:
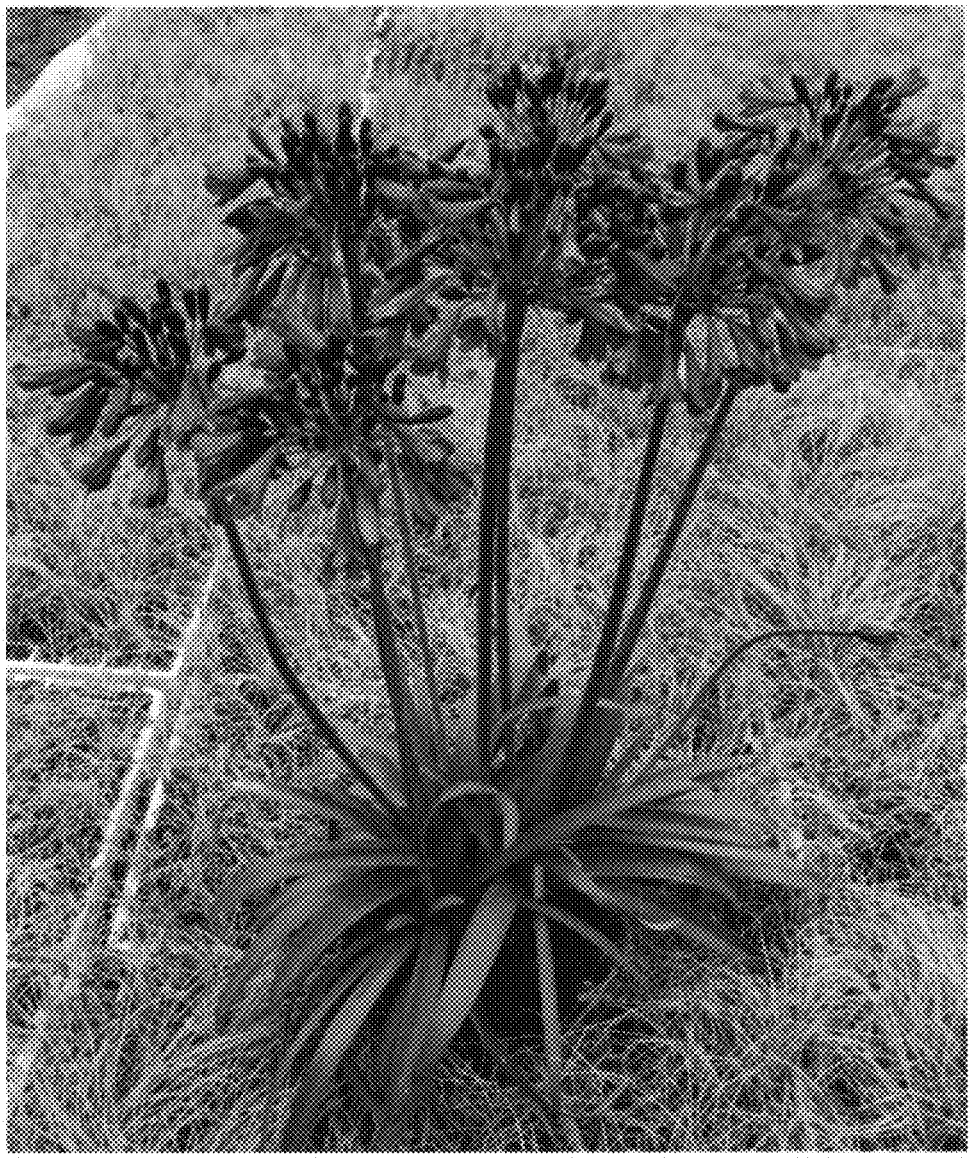
Figure 2:
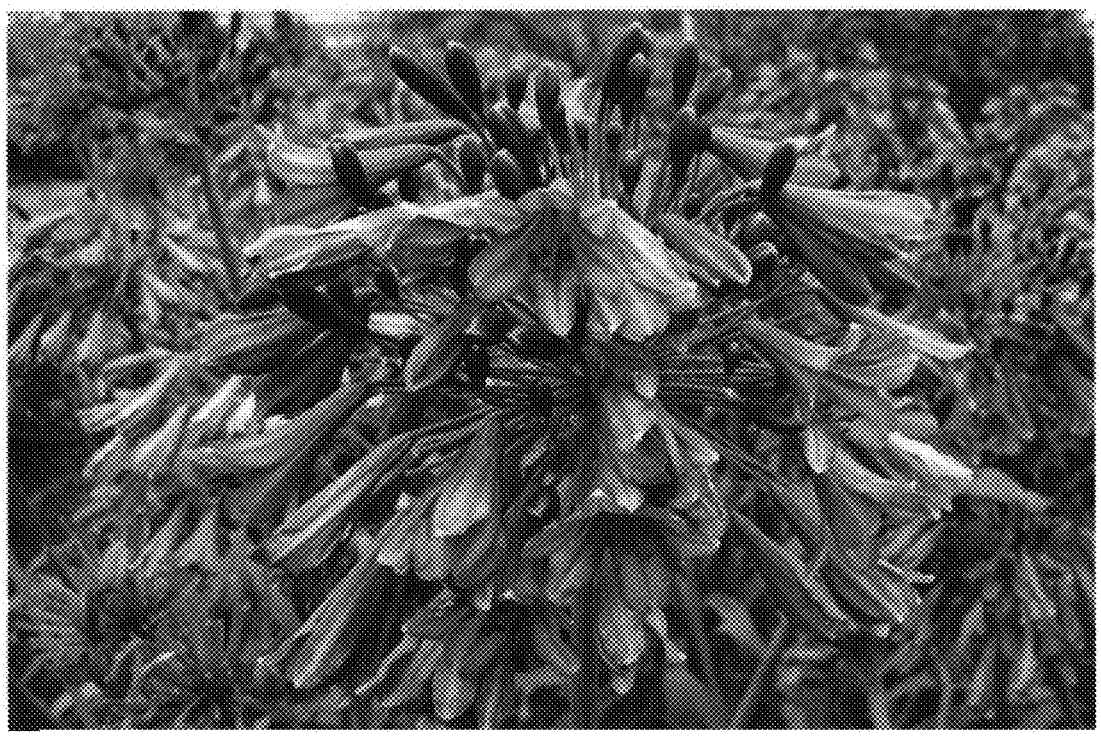

The photograph in FIG. 2 provides a close-up view of an inflorescence of 'MP003'.

The colors in the photographs are as close as possible with the photographic and printing technology utilized and color values cited in the detailed botanical description accurately describe the colors of the new *Agapanthus*.

DETAILED BOTANICAL DESCRIPTION

The following is a detailed description of 1 year-old plants (from a bare root division) of 'MP003' as grown outdoors in 3-gallon containers in Loxley, Ala. The phenotype of the new cultivar may vary with variations in environmental, climatic, and cultural conditions, as it has not been tested under all possible environmental conditions. The color determinations are in accordance with The 2015 R.H.S. Colour Chart of The Royal Horticultural Society, London, England, except where general color terms of ordinary dictionary significance are used.

General description:

*Blooming period*.—Main blooming period is early to mid summer and re-blooms throughout the year in South Africa.

*Plant type*.—Semi-deciduous (climate dependent) herbaceous perennial.

*Plant habit*.—Compact with broad, short leaves emerging from basal rosettes with inflorescences emerging from the rosette centers.

*Height and spread*.—30 to 40 cm in height (foliage), 50 to 60 cm in height (including inflorescences) and 45 to 50 cm in spread.

*Cold hardiness*.—At least to U.S.D.A. Zone 8.

*Diseases*.—Good resistance has been observed to root and crown rot caused by *Fusarium* sp. and soft rot caused by *Erwinia* sp.

*Root description*.—Thick and fleshy, 145D in color.

*Propagation*.—Tissue culture (preferred) and division.

*Growth rate*.—Vigorous.

*Number of shoots (rosettes)*.—An average of 10 as grown in a 3-gallon container.

Foliage description:

*Leaf shape*.—Ligulate.

*Leaf division*.—Simple.

*Leaf base*.—Truncate.

*Leaf arrangement*.—2-ranked, arranged in shoots an average of 2.5 cm diameter at base.

*Leaf apex*.—Narrow acute.

*Leaf aspect*.—Emerging leaves erect, then cascade.

*Leaf venation*.—Parallel, upper surface; matches leaf coloration, and lower surface; with only mid rib conspicuous; a color between 144B and 138B.

*Leaf margins*.—Entire.

*Leaf size*.—Up to 42 cm in length and 2.5 cm in width.

*Leaf surface*.—Smooth, glabrous, and dull on upper and lower surface.

*Leaf number*.—Average of 10 leaves per rosette.

*Leaf color*.—Young leaves, upper and lower surface; 144C and blending to N137B near apex and 145D at base, mature leaves upper surface; 137A and 145D near base with very base N155A and slightly suffused with N82B, mature leaves lower surface; 137A and 145D near base with very base heavily suffused with N82A with margins N92A.

*Leaf attachment*.—Sessile to base.

Flower description:

*Inflorescence type*.—Dense umbel.

*Flower fragrance*.—None.

*Flower type*.—Rotate, campanulate, base of tepals fused.

*Flower number*.—An average of 70 flowers per umbel.

*Inflorescence size*.—Average of 13 cm in height and 16 cm in diameter.

*Flower size*.—An average of 3.9 cm in depth and 3.6 cm in diameter.

*Flower type*.—Tubular-campanulate.

*Lastingness of inflorescence*.—About one month, flowers an average of 7 days.

*Flower aspect*.—Outward to drooping.

*Peduncle*.—Very strong, oval in shape, held primarily upright, up to 68 cm in length and 1.5 cm in width at proximal region and 1 cm in width at distal region, a blend of 144A and 144B in color with base 145C and slightly suffused with N92A, satiny, glabrous and slightly glaucous surface.

*Pedicels*.—Very strong, average of 4.5 cm in length and 1.5 mm in width, held erect to outward (0° to 180°), 144C in color, glabrous surface.

*Flower buds*.—Obelliptic in shape, average of 1.7 cm in length and 6 mm in width, a blend of N82A and 83A just prior to opening, enclosed by 2 to 3 deciduous spathe-like bracts that split open when flowers open; ovate to lanceolate in shape, acuminate apex, truncate base, up to 5.0 cm in length and 2.5 cm in width, color outer surface; a blend of 138A to 138C and suffused with 83C at base, color inner surface; a blend of 138B, 138C and 145C, both surfaces glabrous and dull.

*Tepals*.—Average of 6 (3 inner and 3 outer), oblanceolate in shape, rounded to acute apex of inner tepals rounded with slight notch, apex of out tepals acute, margins are entire and slightly ruffled, lower 25% fused at base, inner and outer surfaces are glabrous and satiny, moderately thick substance, average of 3.9 cm in length, 1 cm in width, inner and outer surface a blend of N88A and N88B in color with a center vein N88A and slight margins of N89A, tube portion is 1 cm in length and 7 mm in width.

Reproductive organs:

*Gynoecium*.—1 pistil, average of 1.9 cm in length, stigma is narrow clavate in shape, minute and 155A in color, style is 1.6 cm in length and 85A in color blending to 155A at base, ovary is oblong in shape, 6 mm in length, 3 mm in width and 150D in color.

*Androecium*.—6 stamens, anthers are dorsifixed, obcordate in shape, average of 1.5 mm in length, and 202A in color, filaments are 2.9 cm in length, adnate to tepal at base and 85A in color blending to 155A at base, pollen is abundant in quantity, 135B in color when mature, a metallic in appearance.

*Fruit/seed*.—Have not been observed to date.

It is claimed:

1. A new and distinct cultivar of *Agapanthus* plant named 'MP003' as herein illustrated and described.

* * * * *